United States Patent [19]

West

[11] Patent Number: 4,671,262

[45] Date of Patent: Jun. 9, 1987

[54] PROSTHETIC DEVICE

[76] Inventor: Boyce W. West, P.O. Box 220, Clarksville, Ark. 72830

[21] Appl. No.: 734,902

[22] Filed: May 16, 1985

[51] Int. Cl.[4] ............................................. A61F 5/41
[52] U.S. Cl. ................................................. 128/79
[58] Field of Search .................. 128/79; 604/349, 351, 604/352

[56] References Cited

U.S. PATENT DOCUMENTS

| | | | |
|---|---|---|---|
| 1,343,951 | 6/1920 | Whyte | 251/321 |
| 2,899,957 | 8/1959 | Briggs | 128/79 |
| 3,683,901 | 8/1972 | Wegener | 128/79 |
| 3,759,254 | 9/1973 | Clark | 128/79 |
| 4,175,554 | 11/1979 | Gerow | 128/79 |
| 4,281,648 | 8/1981 | Rogers | 128/79 |
| 4,378,008 | 3/1983 | Osbon, Sr. | 128/79 |

FOREIGN PATENT DOCUMENTS

| | | | |
|---|---|---|---|
| 148586 | 7/1985 | European Pat. Off. | 128/79 |
| 254211 | 11/1912 | Fed. Rep. of Germany | 128/79 |
| 1497441 | 1/1978 | United Kingdom | 128/79 |

*Primary Examiner*—Robert Peshock
*Assistant Examiner*—Cary E. Stone
*Attorney, Agent, or Firm*—Harvey B. Jacobson

[57] ABSTRACT

A vacuum assisted, semi-rigid prosthetic device for assisting in penile erection in the form of a thin, elongated sheath having an open proximal end to enable insertion of a penis and a closed distal end. The sheath includes a longitudinally extending tubular passageway extending from the proximal end to the distal end with the passageway opening into the interior of the sheath at the distal end. A valve is provided at the proximal end of the sheath for selectively communicating the passageway with a vacuum source to control and regulate the negative pressure within the sheath and a seal is provided on the proximal end of the sheath for sealing engagement with the surface area of a user adjacent the base of the penis to enable a negative pressure to exist in the sheath with the sheath being dimensioned to completely receive a flaccid penis therein and enabling enlargement to a normal erection without pain or limitation with the negative pressure providing semi-rigidity to the sheath to facilitate coitus.

1 Claim, 4 Drawing Figures

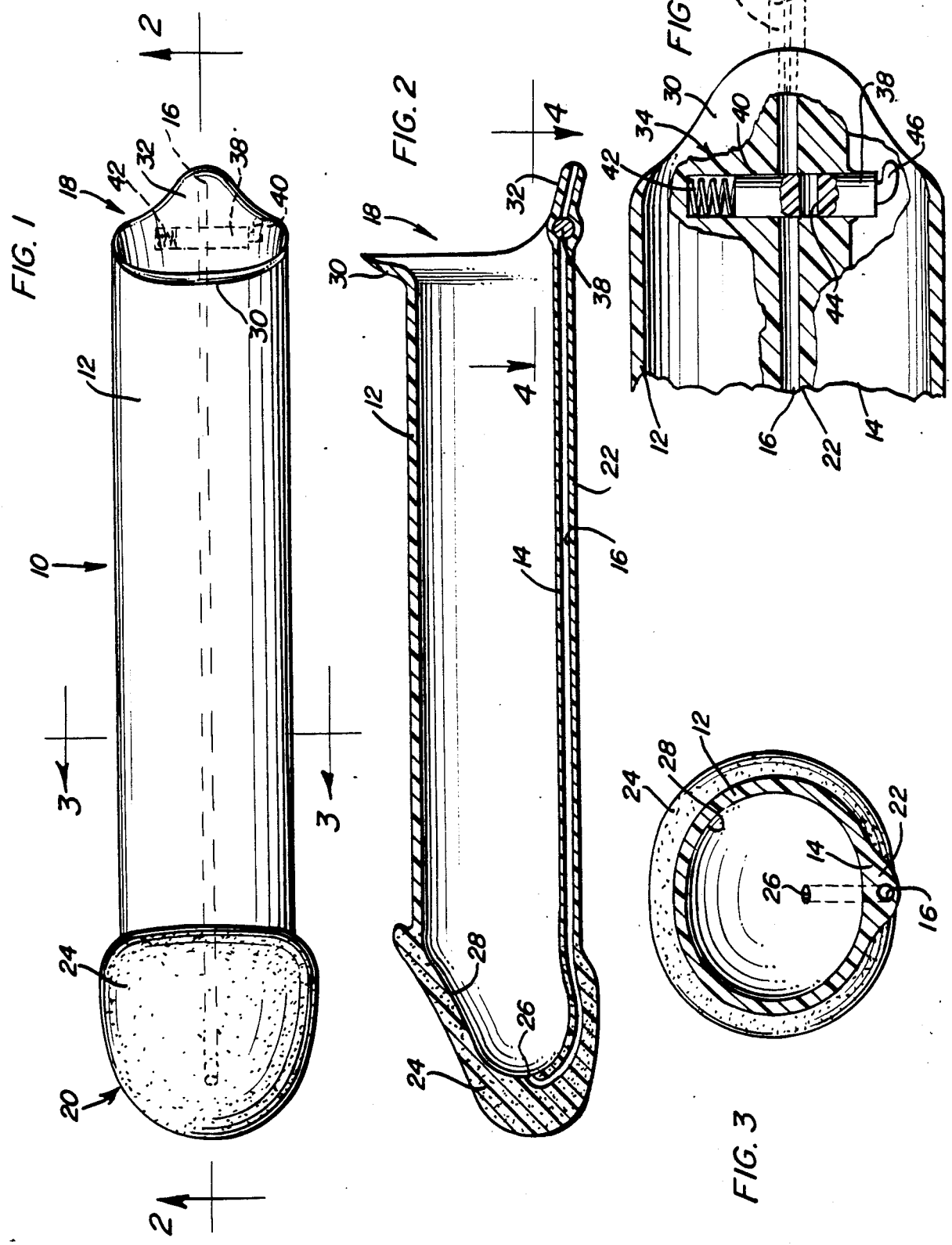

PROSTHETIC DEVICE

BACKGROUND OF THE INVENTION

1. Field of the Invention

The present invention generally relates to a prosthetic device and more specifically a vacuum assisted, semi-rigid, penile prosthesis which utilizes a physiologic basis in assisting in obtaining a natural penile erection. The device includes a sheath constructed to enable total insertion of a flaccid penis with negative pressure or vacuum being applied at the distal end and a flange at the proximal end sealingly engaging the surface of adjacent body areas and exerting pressure thereon simulative of the physiologic closing of the corpora to facilitate a near normal erection with the prothesis enabling enlargement of the penis therein in a normal manner without limitation.

2. Information Disclosure Statement

Male impotence due to physiologic and/or psychologic reasons has been and continues to be an ongoing problem that interferes with satisfactory coitus. In view of the existence of this problem, many efforts have been made to assist a male in obtaining penile erection with the following U.S. patents illustrating the development in this field of endeavor.

U.S. Pat. No. 3,495,589; 2/17/70
U.S. Pat. No. 3,683,901; 8/15/72
U.S. Pat. No. 4,175,554; 11/27/79
U.S. Pat. No. 4,378,008; 3/29/83
U.S. Pat. No. 4,407,275; 10/4/83

While such devices attempt to alleviate the problem of impotence, there still exists a need for an effective prosthetic device which obtains near normal erection by utilizing the physiologic basis for obtaining penile erection.

SUMMARY OF THE INVENTION

An object of the present invention is to provide a prosthetic device in the form of a vacuum assisted, semi-rigid, penile prosthesis utilizing a physiologic basis to obtain a normal or near normal penile erection with the device including a sheath constructed of material which is simulative of the skin, a simulative glans at the distal end and a flange at the proximal end which sealingly engages against the symphysis pubis so that as a vacuum is applied, the flange exerts gentle pressure at the base of the penis causing reflex and physiologic closing of the valves of the corpora thereby facilitating a near normal erection with the sheath being of sufficient size to enable total insertion of the flaccid penis so that it can enlarge inside the prosthesis in a normal manner without pain or limitation.

Another object of the invention is to provide a prosthetic device in accordance with the preceding object constructed in a manner to reduce or eliminate pain and psychological objections to mechanical devices by providing a device that has the appearance and feel of a natural erect penis thereby enhancing its chance of aiding in satisfactory coitus with the device being mutually advantageous to both the male and female.

A further object of the invention is to provide a prosthetic device in accordance with the preceding objects capable of being manufactured in various sizes to permit custom fitting to the normal size of the penis of a user for comfort of both the male and female, constructed in the same shape as an erect penis, capable of being provided with a covering sheath if desired, relatively inexpensive to manufacture, psychologically and physiologically beneficial in obtaining a near normal penile erection, safe in use and satisfactory in use.

These together with other objects and advantages which will become subsequently apparent reside in the details of construction and operation as more fully hereinafter described and claimed, reference being had to the accompanying drawings forming a part hereof, wherein like numerals refer to like parts throughout.

BRIEF DESCRIPTION OF THE DRAWINGS

FIG. 1 is a plan view of the prosthetic device of the present invention.

FIG. 2 is a longitudinal, sectional view taken substantially upon a plane passing along section line 2—2 on FIG. 1 illustrating the structural details of the device.

FIG. 3 is a transverse, sectional view taken substantially upon a plane passing along section line 3—3 on FIG. 1 illustrating further structural details of the device.

FIG. 4 is a fragmental plan view, on an enlarged scale, with portions broken away, illustrating the vacuum control valve at the proximal end of the device and which is located in the inferior wall.

DESCRIPTION OF THE PREFERRED EMBODIMENT

Referring now specifically to the drawings, the prosthetic device of the present invention is generally designated by the reference numeral 10 and includes an elongated tubular sheath 12 of generally cylindrical or oval shaped configuration which is constructed of various diameters and length dimensions to fit and accommodate penises of different sizes to enable erection of the penis within the sheath without pain or limitations. The inferior wall 14 of the tubular sheath 12 is provided with an elongated continuous passageway 16 therein which extends from the proximal end 18 of the sheath to the distal end 20 thereof. As illustrated in FIG. 3, the inferior wall 14 has the passageway 16 formed in a thickened portion or downwardly projecting longitudinal portion 22 of the inferior wall so that the interior surface of the sheath 12 will be smooth and continuous.

The distal end of the sheath 12 is provided with a thickened and enlarged but yet relatively soft enlarged body portion 24 which is closely simulative of the glans penis of a normal erect penis. The passageway 16 continues along the interior of the inferior wall 14 of the sheath 12 and into the body portion 24 terminating in an opening 26 generally at the center of the interior wall 28 of the glans penis 24.

The proximal end 18 of the sheath 12 is provided with a flange 30 across the superior wall and extending partially down the side walls with the inferior wall 14 including a longer flange 32 which extends axially and flares downwardly slightly as illustrated in FIG. 2 whereas the flange 30 curves radially outwardly so that the flanges 30 and 32 conform with, fit and sealingly engage the symphysis pubis at the base of the penis with a lubricant being used to provide a more effective seal. The flange 32 includes the passageway 16 and a vaccum valve assembly 34 to control the negative pressure or vacuum from a vaccum source or tube 36. The valve assembly 34 includes a transversely disposed valve member 38 slidably disposed in a transverse passageway 40 which communicates with the passageway 16 and extends laterally in the projecting flange 32 as illustrated in FIG. 4. A spring 42 engages the inner end of the valve member and the inner closed end of the passageway 40 to retain a passageway 44 in the valve member 38 in misalignment with the passageway 16 with the outer end of the valve member 38 projecting outwardly from the flange 32 so that inward pressure on the outer end of the valve member 38 will move it inwardly to bring the passageway 44 into alignment with the passageway 16 to enable regulation of the negative pressure in the passageway 16. The outer end of the valve 38 may be provided with a lateral projection 46 forming a handle for more effective manipulation of the valve member 38.

The sheath 12 may be constructed of a soft "skin-like" latex, semi-rigid polyethylene or similar synthetic non-irritating or corrosive material constructed in the shape of an erect male penis so that it is very difficult to distinguish the prosthetic device from a normal erect penis by touch alone. The soft glans penis 26 may be constructed of a foam material and may be inflated with ten to 20 cubic centimeters of air or liquid if desired or necessary to enhance satisfactory coitus and the soft construction of the glans will do no harm even during deep penetration. The distal end is closed and provided with an opening at the termination of the passageway 16 and the proximal end is open with the flange 32 having the vacuum control and release valve assembly 34 incorporated therein with the valve member 38 being closed when at rest. When the valve member 38 is moved to the open position, vacuum will be applied and when released, the valve will close to maintain the vacuum and erection of the penis until detumescence is desired at which time pressure on the vacuum release valve without the source of vacuum being active will allow return to the flaccid state. Variations in pliability and rigidity may be utilized along with variations in the texture of the surface may be utilized and a second tube or passageway parallel to the vacuum tube or passageway 16 will allow the use of an inflatable glans penis. If desired, a latex cover or sheath can be applied with any desired textured surface for more effective massage of the vaginal mucosa and the device may be constructed in different sizes to provide optimum satisfaction for both the male and female during coitus. This device reduces problems caused by impotence and enables paraplegics, handicapped persons, men having transurethral resection of the prostate gland and premature ejaculators to satisfactorily engage in sexual intercourse by enabling the male to obtain and maintain an erection of his own penis for a sufficient time and with sufficient rigidity to engage in coitus. The mechanism of the action of the present invention is consistent with the physiology of a normal unassisted male erection which is obtained by the engorgement of the vessels of the penis with the circulating blood therein. This is obtained by the pressure exerted by the flanges 30 and 32 at the proximal end of the sheath so that as negative pressure is applied to the interior of the prosthesis with a flaccid penis totally inserted therein, the prosthesis will exert gentle pressure at the base of the penis causing reflex and physiologic closing of the valves of the corpora thereby facilitating a near normal erection with the penis being able to enlarge inside the prosthesis in a normal manner without pain or limitation.

The foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as new is as follows:

1. A prosthetic device for assisting in penile erection comprising a thin, elongated, tubular sheath having a smooth interior surface and exterior surface constructed of skin-like film material and having an open proximal end to enable insertion of a penis and a closed distal end, said sheath including an inferior wall and superior wall unitary with sidewall portions and including a longitudinally extending tubular passageway extending from the proximal end to the distal end with the passageway being formed in the inferior wall and opening into the interior surface of the sheath at the distal end, valve means in the passageway at the proximal end of the sheath for selectively communicating the passageway with a vacuum source of negative pressure to control and regulate the negative pressure within the sheath and means on the proximal end of the sheath for sealing engagement with the surface area of a user adjacent the base of the penis to enable a negative pressure to exist in the sheath and to exert gentle pressure at the base of the penis causing reflex and physiologic closing of the valves of the corpora thereby facilitating more normal erection, said sheath being provided with an external projection along the inferior wall in which said passageway is formed thereby providing a continuous smooth interior surface in the sheath, said sheath being dimensioned to completely receive a flaccid penis therein and enabling enlargement to a normal erection without pain or limitation with a negative pressure providing semi-rigidity to the sheath to facilitate coitus, said closed distal end of the sheath including a soft simulative glans penis having an exterior surface and interior surface shaped to simulate a natural glans penis constructed of soft material substantially thicker than and slightly larger in circumference than the portion of the sheath from the proximal end to the simulated glans penis, said passageway extending from an opening in a central area of the interior surface of the simulated glans penis, said simulated glans penis at the distal end having an internal surface shaped to simulate and closely receive a natural glans penis, said means at the proximal end of the sheath for engagement with the surface area adjacent the base of the penis including a flange extending laterally from the superior wall of the sheath and being generally flexible for engagement with the symphsis pubis, the inferior wall of the sheath including an axially and downwardly angled flange having the valve means incorporated therein with the free edge of the flange on the inferior wall including curved edges conforming with and engaging the surface areas adjacent the base of the penis with the flange adapted to receive lubricant to maintain a seal to maintain negative pressure in the sheath when the distal end if communicated with a source of vacuum, said valve means including a transverse passageway at the proximal end of the sheath in communication with the longitudinal passageway, a valve member slidably disposed in the transverse passageway and including an opening therethrough for selective alignment with the longitudinal passageway, a spring in the transverse passageway engaging one end of the valve member and the end of the transverse passageway to bias the valve member toward closed position with respect to the longitudinal passageway for trapping a negative pressure in the sheath with the outer end of the valve member being disposed externally of the sheath to enable manipulation thereof to selectively communicate the interior of the sheath with a vacuum source or release the negative pressure therein to facilitate removal of the prosthetic device from the penis.

* * * * *